(12) United States Patent
O'Leary et al.

(10) Patent No.: US 8,474,732 B2
(45) Date of Patent: Jul. 2, 2013

(54) AIR FRESHENER DEVICE COMPRISING A SPECIFIC LIQUID COMPOSITION

(75) Inventors: Nicholas O'Leary, Pennington, NJ (US); Florin Joseph Vlad, Annandale, NJ (US)

(73) Assignee: Firmenich SA, Geneva (CH)

( * ) Notice: Subject to any disclaimer, the term of this patent is extended or adjusted under 35 U.S.C. 154(b) by 880 days.

(21) Appl. No.: 11/845,566

(22) Filed: Aug. 27, 2007

(65) Prior Publication Data

US 2008/0023569 A1 Jan. 31, 2008

Related U.S. Application Data

(63) Continuation of application No. PCT/IB2006/050702, filed on Mar. 7, 2006.

(60) Provisional application No. 60/664,545, filed on Mar. 23, 2005.

(30) Foreign Application Priority Data

Mar. 24, 2005 (WO) .................. PCT/IB2005/000816

(51) Int. Cl.
*A24F 25/00* (2006.01)
*A61L 9/04* (2006.01)
*A61K 8/00* (2006.01)
*A61K 8/18* (2006.01)
*A61Q 13/00* (2006.01)

(52) U.S. Cl.
USPC .................. 239/44; 239/54; 512/1; 512/3

(58) Field of Classification Search
USPC ...................... 239/44, 53; 512/1, 3
See application file for complete search history.

(56) References Cited

U.S. PATENT DOCUMENTS 4,670,185 A * 6/1987 Fujiwara et al. ............... 516/57
5,047,234 A 9/1991 Dickerson et al. .......... 424/76.2
(Continued)

FOREIGN PATENT DOCUMENTS

| EP | 0 419 850 B1 | 1/1995 |
| EP | 1 502 608 A2 | 2/2005 |
| WO | WO 89/08462 | 9/1989 |
| WO | WO 98/25651 | 6/1998 |
| WO | WO 98/26809 | 6/1998 |
| WO | WO 01/88076 A1 | 11/2001 |
| WO | WO 02/34409 A2 | 5/2002 |
| WO | WO 02/068128 A2 | 9/2002 |
| WO | WO 2004/110559 A1 | 12/2004 |

OTHER PUBLICATIONS

Hydrophilic-lipophilic_balance: http://en.wikipedia.org/wiki/Hydrophilic-lipophilic_balance p. 1.*
Pyrrolidone carboxylic acid PubChem http://pubchem.ncbi.nlm.nih.gov/summary/summary.cgi?cid-499 p. 1-6.*

*Primary Examiner* — Patrick Ryan
*Assistant Examiner* — Aaron Greso
(74) *Attorney, Agent, or Firm* — Winston & Strawn LLP

(57) ABSTRACT

The present invention relates to air freshener devices that have water-based liquid compositions, preferably clear liquids, for providing an improved rate of emanation of perfume ingredients from the air freshener emanating surface and allowing the use of fragrance materials with a wide range of characteristics, namely a wide range of clogP values. The air fresheners contain liquid perfume compositions which include:
i) 0.5 to 40% w/w of a perfume;
ii) an oil-solubilizing system containing one or more surfactants of the non-ionic, anionic, cationic, amphoteric type, or a mixture thereof;
iii) a solubilizing-aid; and
iv) at least 40% weight of water;
with the weight percentages being relative to the total weight of liquid composition.

14 Claims, 6 Drawing Sheets

Comparison of Average Weekly Rate of Emanation over Time of Composition of Example 2C and conventional Composition of Example 1C

U.S. PATENT DOCUMENTS

| | | | |
|---|---|---|---|
| 5,081,104 A * | 1/1992 | Orson, Sr. | 512/3 |
| 5,290,547 A | 3/1994 | Bilbrey | 424/76.6 |
| 5,374,614 A * | 12/1994 | Behan et al. | 512/3 |
| 6,766,817 B2 | 7/2004 | da Silva | 137/1 |
| 6,918,404 B2 | 7/2005 | Dias da Silva | 137/132 |
| 7,066,586 B2 | 6/2006 | da Silva | 347/85 |
| 2001/0044392 A1 | 11/2001 | Trinh et al. | 510/101 |
| 2003/0146294 A1 * | 8/2003 | Minamite et al. | 239/44 |
| 2003/0207988 A1 * | 11/2003 | Tamareselvy et al. | 524/800 |
| 2004/0037792 A1 * | 2/2004 | Hiramoto et al. | 424/65 |
| 2004/0209795 A1 * | 10/2004 | Vlad | 512/4 |

* cited by examiner

Figure 3 - Comparison of Cumulative Weight Loss over Time of Composition of Example 2B and conventional Composition of Example 1B Figure 4 – Comparison of Average Weekly Rate of Emanation over Time of Composition of Example 2B and conventional Composition of Example 1B Figure 5 - Comparison of Cumulative Weight Loss over Time of Composition of Example 2C and conventional Composition of Example 1C

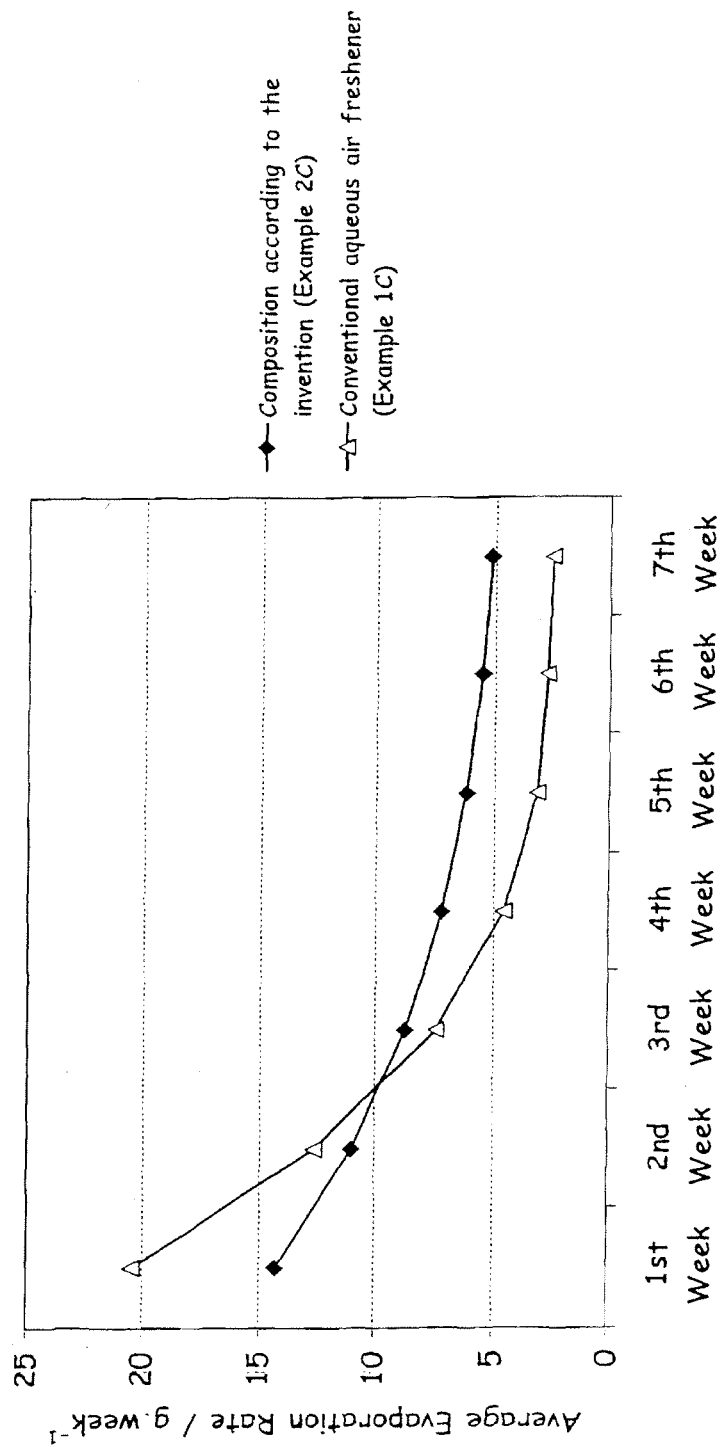
Figure 6 – Comparison of Average Weekly Rate of Emanation over Time of Composition of Example 2C and conventional Composition of Example 1C

AIR FRESHENER DEVICE COMPRISING A SPECIFIC LIQUID COMPOSITION

CROSS-REFERENCE TO RELATED APPLICATIONS

This application is a continuation of International application PCT/IB2006/050702 filed Mar. 7, 2006 which claims the benefit of application 60/664,545 filed Mar. 23, 2005. The entire content of each application is expressly incorporated herein by reference thereto.

TECHNICAL FIELD

The present invention relates to air freshener devices comprising water-based liquid compositions, preferably clear liquids, that provide an improved rate of emanation of perfume ingredients from the air freshener emanating surface and allow the use of fragrance materials with a wide range of characteristics, namely a wide range of clogP values.

The invention also concerns air freshener devices based on the use of such compositions and which comprise an emanating surface providing for diffusion of the perfume and a wick system for supplying the liquid to the emanating surface.

BACKGROUND

Conventional air fresheners diffusing a liquid perfume composition which is brought to an emanating surface via a wick system generally comprise a reservoir containing the fragrance composition, into which dips the wick, the latter being connected to the emanating surface. It is also quite common for the wick and the emanating surface to be part of a same component of the air freshener device. The perfume composition travels up the wick to the emanating surface, from which the perfume evaporates to freshen the surrounding atmosphere. The fragrance composition may be a true solution, a colloidal solution or a microemulsion.

Air freshener systems in which the perfume solution is aqueous-based usually contain a surface active agent to solubilize the perfume in the water. In order to achieve the desired clarity of the composition to be diffused, the products contain a surfactant system that is generally largely in excess with respect to the perfume. Typically, the ratio of surfactant to perfume is of at least 1.5, more typically between 2 and 2.5. As such surface active agents are non-volatile, they do not evaporate from the emanating surface. Moreover, the concentration of surfactant in the emanating surface gradually increases, and this in turn results in a reduced rate of perfume evaporation. There is therefore a perceivable decrease in odor intensity during the usage of the product.

Some known aqueous air fresheners contain no surfactant. U.S. Pat. Nos. 4,663,081 and 6,180,595 describe surfactant-free compositions intended for air fresheners. However both examples describe compositions that contain high levels (30 to 60% w/w) of organic solvents, which is also undesirable.

U.S. Pat. No. 4,663,081 claims that diethylene glycol monobutyl ether (DEGMBE) can, when containing dissolved perfume, incorporate a surprisingly large quantity of water compared to other glycol ethers. However, in view of the toxicity problems associated with DEGMBE, it is apparent that another solution is required.

U.S. Pat. No. 6,180,595 sets out to address the aforementioned problem. It describes compositions that contain between 30 and 60% w/w of a mixture of two glycol ether components. It also states however that the perfume composition must comprise at least 60% w/w of fragrance components having a cLogP not above 2.5. Since many perfumery ingredients useful in the field of air fresheners have a cLogP>2.5, this limitation represents a serious constraint in the creation of air freshener perfume compositions. Furthermore the ratio of organic solvent to perfume, given in the examples, is typically around 4, and thus such compositions are not very cost effective.

There is therefore still a need for a clear liquid fragrance composition containing low levels of oil-solubilizers or surfactants, so as to minimize clogging of the wick and emanating surfaces, that can effectively solubilize a wide range of fragrance ingredients regardless of their cLogP and that is non-toxic and safe to use.

It is the precisely the object of the present invention to provide such a composition and air freshener devices containing it.

SUMMARY OF THE INVENTION

The invention relates to an air freshener device for perfuming or freshening the surroundings thereof, which comprises a liquid fragrance composition contained in a vessel, means to carry the liquid composition from the containing vessel to an emanating surface from which the composition can be diffused into the surroundings, and optionally means to prevent such diffusion before desired activation of the device, wherein said liquid composition comprises:
i) 0.5 to 40% w/w of a perfume;
ii) an oil-solubilising system containing one or more surfactants of the non-ionic, anionic, cationic, amphoteric type, or a mixture thereof;
iii) a solubilizing-aid; and
iv) at least 40% weight of water;
weight percentages being relative to the total weight of liquid composition.

The invention further concerns a method of use of the above-mentioned liquid composition and air freshener device to confer, improve, modify or enhance the odor of, and/or freshen, the air surrounding said composition and air freshener device, in rooms and open spaces, closets, cupboards and other closed environments.

BRIEF DESCRIPTION OF THE DRAWINGS

FIG. 6 shows the average weekly rate of emanation of a composition according to the invention (of Example 2C)

Figure 1:
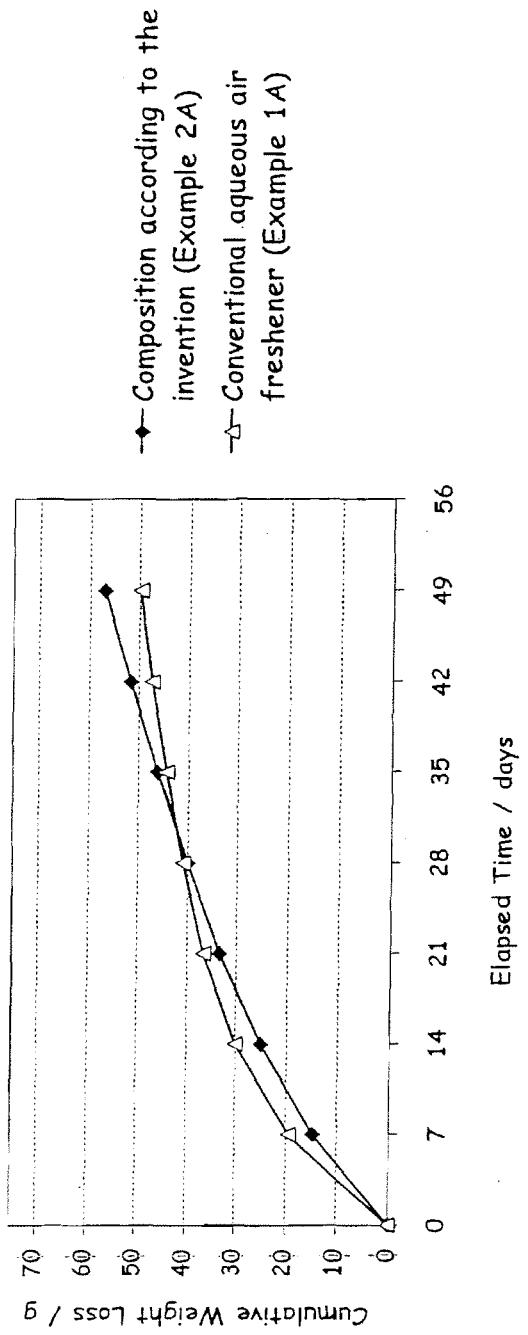
FIG. 1 shows the cumulative weight loss of a composition according to the invention (of Example 2A) compared to a conventional aqueous based air freshener (of Comparative Example 1A) over a period of time.

compared to a conventional aqueous based air freshener (of Comparative Example 1C) over a period of time.

DETAILED DESCRIPTION OF THE PREFERRED EMBODIMENTS

The invention provides an air freshener device for perfuming or freshening the surroundings thereof, which comprises:
a) a vessel carrying a liquid composition which contains:
   i) 0.5 to 40% w/w of a perfume;
   ii) an oil-solubilizing system containing one or more surfactants of the non-ionic, anionic, cationic, amphoteric type, or a mixture thereof; and
   iii) at least 40% weight of water; weight percentages being relative to the total weight of liquid composition;
b) an emanating surface capable of providing for diffusion of said liquid composition;
c) means for carrying the liquid composition from the container vessel to the emanating surface; and
d) optionally, removable means for preventing diffusion of the liquid composition prior to the activation of the air freshener device by a user thereof;
wherein said liquid composition further comprises a solubizing-aid ingredient.

According to one embodiment of the invention the solubilizing-aid is present in the liquid composition in a concentration of from 0.01 to 10% w/w, relative to the total weight of liquid composition, and the ratio of oil-solubilizing system to perfume is between 0.3 and 1.4.

According to another embodiment, the solubilizing-aid ingredient is selected from the group consisting of the ammonium, alkaline and alkaline earth salts of:
i) a $C_5$-$C_{10}$ compound comprising an aromatic or non aromatic five or six member heterocyclic ring and one or two carboxylic functional groups;
ii) a $C_2$-$C_7$ linear, branched or cyclic mono-, di- or tri-carboxylic acid;
iii) benzoic, hydroxyl-benzoic or amino-benzoic acid, a $C_8$-$C_{12}$ benzoic, hydroxyl-benzoic or amino-benzoic acid substituted by one or two $C_1$-$C_5$ alkyl groups;
iv) benzene-sulfonic acid, a $C_7$-$C_{11}$ benzene-sulfonic acid substituted by one or two $C_1$-$C_5$ alkyl groups, optionally hydroxylated naphthalene-sulfonic acid, an optionally hydroxylated naphthalene-sulfonic acid substituted by one or two $C_1$-$C_5$ alkyl groups;
v) a halide, ascorbate, bicarbonate, thiocyanate; and
vi) mixtures thereof;

The above liquid composition is a clear, water-based, fragrance composition intended to be diffused in closed spaces such as cupboards, drawers and closets, or into the surrounding environment of air freshener devices, such as open spaces and rooms. The composition is particularly adapted for use in wick-type air freshener devices and it does not suffer from the prior known deficiencies mentioned above.

We have now surprisingly discovered that the use of a suitable amount of an appropriate solubilizing-aid ingredient, in addition to the classical ingredients of the aqueous air freshener compositions such as the perfume, the surfactant system and water, can solve the problems encountered previously with known air fresheners.

According to a particular embodiment of the air freshener of the invention, the perfume composition is carried into the emanating surface via a wick.

As mentioned above, in a particular embodiment of the invention, the liquid composition for the air freshener device is more preferably formed of an isotropic, thermodynamically stable, nano-dispersion comprising:

a) 0.5 to 40% w/w of a perfume;
b) an oil-solubilizing system containing one or more surfactants of the non-ionic, ionic or amphoteric type, or a mixture thereof, wherein the weight ratio of solubilizing system to perfume is between 0.3 and 1.4;
c) 0.01 to 10% w/w of a solubilizing-aid ingredient; and
d) at least 40% weight of water.

By a "composition for an air freshener device" it is meant here a composition that is in a form appropriate to be diffused into its surroundings via an air freshener device of the wick type. The composition may therefore also comprise optional ingredients such as thickeners, anti-oxidants, dyestuffs, bittering agents, UV inhibitors, preservatives, chelating agents and any other appropriate oil or water soluble ingredients.

Following particular embodiments of the invention, the w/w ratio of oil-solubilizing system to fragrance is below 1.

In the definition above, the abbreviation w/w represents weight-to-weight ratio, meaning the ratio between the weight of a specific ingredient and the weight of the liquid composition.

Moreover, from heretofore, the ratio perfume oil/(oil-solubilizing system+solubilizing-aid ingredient) shall be designated as the "O/(S+SA)" ratio.

In contrast to the classical micellar solubilization systems based on short- and/or medium-chain alcohols or non-ionic surfactants as co-surfactants, the specific solubilization systems of the invention above-mentioned can solubilize any fragrance, at any concentration between 0.5% and up to 40% w/w, more preferably up to 20 or 30% w/w, without changing the surfactant system, unlike what was the case with the prior known solubilizing systems.

By "nano-dispersion" we mean here a dispersion that forms spontaneously and has a droplet size comprised between 10 and 150 nm, at a temperature comprised between 0° and 80° C. However, according to a particular embodiment of the invention, the present liquid composition has a droplet size comprised between 10 and 60 nm, or even between 10 and 40 nm, at a temperature comprised between 0° and 80° C.

The invention thus provides an air freshener device comprising a container for carrying the liquid fragrance composition such as above-mentioned, means for transporting this composition to a diffusing or emanating surface from which the composition is diffused into its surroundings, upon activation of the air freshener device by a user. When necessary, e.g. during storage of the non-activated air freshener device, the latter also comprises means for preventing evaporation of the fragrance composition prior to activation of the air-freshener by the user, which means are removable to allow activation of the device when desired.

The liquid composition contains 0.5 to 40% by weight of a perfume or fragrance. By a "perfume" or a "fragrance" it is meant here an ingredient, or a mixture of ingredients, which are primarily intended to impart a perfume to and/or freshen the surroundings of the air-freshener device. This is typically a lipophylic organic liquid that is essentially insoluble in water. An example of a suitable oil to be solubilized is a liquid that comprises at least 75% w/w, or even at least 90% w/w, of a perfume or a perfuming composition.

In particular, as the perfume or perfuming composition there can be used any perfuming ingredient or, as happens more often, any mixture of perfuming ingredients currently used in perfumery, e.g. of compounds capable of imparting pleasant odor to the air or closet surroundings of the air-freshener. Said perfuming ingredients can be of natural or synthetic origin. A detailed description of said ingredients would not be warranted here and, in any case, it cannot be exhaustive. Generally speaking, it can be mentioned that these ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin. The nature of these ingredients can be found in specialized books of perfumery, e.g. in S. Arctander (Perfume and Flavor Chemicals, Montclair N.J., USA 1969 or later versions thereof), or similar textbooks of reference, and a more detailed description thereof is not warranted here. The selection of such ingredients is carried out by the perfumer without particular difficulty, on the basis of her/his general knowledge and as a function of the desired sensory effect, i.e. the perfuming effect that is to be imparted to environing surroundings.

As previously mentioned, the nature of the perfume ingredients is totally immaterial for the intended effect of the compositions and devices of the invention. As a result of the presence of the solubilizing-aid ingredient or ingredients in the liquid composition of the invention, it is possible to solubilize any perfume ingredient, or mixture of ingredients, regardless of the clogP values thereof.

Therefore, it is possible to use, as the solubilized oil, low polarity oils, in particular a low polarity perfume. By "low polarity oil or perfume" we mean here, for example, an oil or perfume rich in highly hydrophobic ingredients or an oil or perfume that contains only small amounts of polar solvents or is completely free of polar solvents.

As low polar perfumes one can mention those containing from 5% w/w, or even 20% w/w, to 99% w/w of terpenes and/or from 5 to 30% w/w of musks; percentages being relative to the weight of the solubilized perfume oil.

Said terpenes may be of wood or citrus origin and example of which are terpineol. or d-limonene. A non-restrictive example of musks is hexadecanolide or HABANOLIDE® (15-pentadec-11,12-enolide; origin: Firmenich SA, Geneva, Switzerland).

As mentioned above, the perfume oil represents between 0.5 to 40% of the liquid nano-dispersion total weight. According to particular embodiments the oil content represents preferably from 5 to 20% w/w, relative to the liquid composition total weight.

The perfume may also contain a suitable solvent, in a quantity of up to 25% w/w of the perfume oil, but preferably less than 10% w/w. The presence of a solvent may be useful to obtain a monophasic oil or to modulate the surface tension of said oil. As examples of suitable solvents, one may cite polar or non-polar low molecular weight solvents such as isoparaffins, paraffins, hydrocarbons, silicon oils, perfluorinated aliphatic ethers, glycol ethers, glycol ether esters, esters, or ketones. Non-restrictive examples of such solvents include dimethicone or cyclomethicone, which are commercialized by Chemsil Silicon Inc. under the trade names COSMETIC FLUID® 1288, and respectively COSMETIC FLUID® 1387, jojoba oil, perfluoroisobutyl methyl ether, diethyl phthalate, dipropylene glycol and isopropyl myristate.

The liquid composition of the present invention also comprises an oil-solubilising system, typically designated as a surfactant system. This oil-solubilizing system may be non-ionic, anionic, cationic, amphoteric or a mixture of two or more such surface active agents.

Suitable anionic solubilizers comprise the salts of $C_6$-$C_{24}$ mono- or di-sulfonic, alkylsulfuric, alkylarylsulfuric, alkylarylphosphate or carboxylic acids and also the polyethylene glycol co-polymers with sulfonic or carboxylic acids. Specific, but not limiting examples of said anionic surfactants are sodium, potassium, ammonium or mono-, di- or tri-ethanolammonium salts of $C_6$-$C_{12}$ dialkyl sulfosuccinic acids (such as sodium dioctyl-sulfosuccinate), $C_7$-$C_{24}$ alkarylsulfonic acids (such as sodium dodecyl benzenesulfonate), $C_6$-$C_{15}$ alkylsulfuric acid (such as sodium dodecylsulfate), $C_{10}$-$C_{20}$ acyl glutamic acid (such as sodium cocoyl glutamate), or polyethylene glycol/dimethicone sulfosuccinic acids (such as disodium PEG-12 dimethicone sulfosuccinate known under the trade name MACKANATE® DC-50 from The McIntyre Group).

Suitable cationic solubilizers comprise the salts of $C_{10}$-$C_{35}$ ammonium derivatives of fatty acids, alcohols, alkylamidoalkylmorpholine or amines and also the IPDI (isophorone diisocyanate) co-polymers with said ammonium derivatives or with fatty amines and optionally polyethylene glycols. Specific, but not-limiting examples, of said cationic surfactants are halides, sulfates or carboxylates of $C_{20\text{-}30}$ quaternary ammonium alkyl (such as hexadecyltrimethyl ammonium bromide or didodecylammonium bromide), $C_{1\text{-}4}$ alkyl N-cocoyl-L-arginate (such as DL-2-pyrrolidone-5-carboxylic acid salt of ethyl N-cocoyl-L-arginate commercialized by Ajinomoto Co., Inc. under the trade name CAE®), ($C_{10\text{-}20}$ amido) ($C_{1\text{-}4}$ alkyl) morpholine (such as isostearamidopropyl morpholine lactate), IPDI copolymers with N—$C_{10\text{-}20}$amido ($C_{1\text{-}4}$ alkyl)-N,N-di($C_{1\text{-}4}$ alkyl)-N—($C_{1\text{-}4}$ alkyl) Ammonium (such as bis(N-Ricinolemidopropyl-N,N-Dimethyl)/N-Ethyl Ammonium Sulfate/IPDI Copolymer also known under the trademark POLYQUAT® PPI-RC from ALZO) or polyethylene glycol/$C_{10}$-$C_{20}$ fatty alkyl amine/IPDI copolymers (such as the PEG Cocamine/IPDI Copolymeric surfactants also known under the trademark POLYDERM® PPI-CA-15 from ALZO).

Suitable amphoteric solubilizers comprise $C_{10}$-$C_{25}$ betaines, amphoacetates and imidazoline derivatives, as well as the polyethylene glycol/fatty amine/glycine/IPDI copolymers. Specific, but non limiting, examples of said amphoteric surfactants are the C $C_{20}$ fatty amido $C_2$-$C_5$ alkyl betaines (such as cocoamidopropyl betaine), coco- and lauro-amphoacetates (such as sodium cocoamphoacetate known under the trade name MACKAM® HPC-32 commercialized by McIntyre Group), and the polyethylene glycol/$C_{10}$-$C_{20}$ fatty alkyl amine/glycine/IPDI copolymers (such as PEG-13 soyamine-Glycine/IPDI Copolymer also known under the trademark POLYTAINE® PPI-SA-15 from ALZO).

Suitable examples of non-ionic solubilizers include ethoxylated and/or propoxylated ($C_5$-$C_{12}$ alkyl)phenols ethers containing 5 to 20 EO or PO units (such as polyethylene glycol nonylphenyl ethers, polyethylene glycol octylphenyl ethers, also known under the generic tradename POLYSTEP®), polyethylene glycol sorbitol ether containing 3 to 30 EO units (such as sorbitol esters with oleic, myristic, stearic, palmitic acid also known as those known under the tradenames TWEEN® from ICI or GLYCOSPERSE® from LONZA), sucrose esters with $C_8$-$C_{20}$ fatty acid (such as sucrose esters with oleic, palmitic or stearic acid, such as Ryoto Sugar Ester M-1695 commercialized by Mitsubishi-Kagaku Foods Corporation), ethoxylated aliphatic $C_6$-$C_{20}$ alcohols containing 2 to 30 EO units (such as ethoxylated secondary $C_6$-$C_{20}$ alcohols), $C_8$-$C_{20}$ polyglyceryl esters (such as glycerol-polyethylene glycol oxystearate commercialized by BASF under the trade name CHROMOPHOR® CO40), polyethylene glycol and polypropylene glycol block copolymers (such as those known under the tradename PLURONICS® from BASF), ethoxylated glycol ether containing 2 to 30 EO units (such as PEG-10 stearyl ether also known under the trade name VOLPO® S-10 from CRODA), or polyethylene glycol mono- or di-ester of aliphatic $C_5$-$C_{11}$ carboxylic acids containing 2 to 10 EO units (EO stands for ethylene oxide and PO stands for propylene oxide).

In all embodiments of the invention the ratio of oil-solubilizing or surfactant system versus the liquid perfume is kept to as low a value as possible, and preferably below 1, in order to avoid the above-cited ill-effects associated with large contents of surfactant or oil-solubilizer which tend to cause clogging of the wick and emanating surfaces of the air-freshener or room deodorant.

Moreover, the weight ratio (perfume/oil-solubilizer system) in the liquid composition can be kept constant for all concentrations of perfume or flavor, meaning that it can be kept independent from the amount of perfume that one wants to solubilize.

In fact, the presence of the solubilizing-aid ingredient in the liquid compositions according to the invention makes it possible to vary at will the concentration of perfume oil, as well as the amount of water in the water phase thereof, without touching the oil/solubilizing system ratio, and this for any type of fragrance, by varying the solubilizing-aid ingredient concentration and nature as a function of the perfume oil.

By the expression "solubilizing-aid ingredient" we mean here an organic or inorganic salt, or a precursor thereof, of low molecular mass, e.g. below 400 g/mol. As solubilizing-aid ingredient it can also be used a mixture of said salts.

As previously mentioned, this is an ingredient selected from the group consisting of the ammonium, alkaline and alkaline earth salts of:
i) a $C_5$-$C_{10}$ compound comprising an aromatic or non aromatic five or six member heterocyclic ring and one or two carboxylic functional groups;
ii) a $C_2$-$C_7$ linear, branched or cyclic mono-, di- or tri-carboxylic acid;
iii) benzoic, hydroxyl-benzoic or amino-benzoic acid, a $C_8$-$C_{12}$ benzoic, hydroxyl-benzoic or amino-benzoic acid substituted by one or two $C_1$-$C_5$ alkyl groups;
iv) benzene-sulfonic acid, a $C_7$-$C_{11}$ benzene-sulfonic acid substituted by one or two $C_1$-$C_5$ alkyl groups, optionally hydroxylated naphthalene-sulfonic acid, an optionally hydroxylated $C_{11}$-$C_{16}$ naphthalene-sulfonic acid substituted by one or two $C_1$-$C_5$ alkyl groups;
v) a halide, ascorbate, bicarbonate, thiocyanate; and
vi) mixtures thereof;

Said compounds, which per their nature are neither surfactants nor solvents, have been found to improve the solubility of organic compounds in water. In fact, and unexpectedly, these salts, or their precursors, are able to enhance the oil-solubilization capacity of the oil-solubilizing system. In other words, in the presence of a solubilizing-aid ingredient, as defined above or below, the same amount of surfactant is able to solubilize in the water phase more oil than if the solubilizing-aid ingredient was not present. It is therefore possible to obtain, for specific perfume concentrations, liquid compositions according to the invention wherein the amount of oil-solubilizing system is below that which would normally have been necessary for the same perfume concentration. This makes it possible to reduce the amount of surfactant or oil-solubilizing system and thus improve the clarity of the liquid composition as well as the diffusion of the perfume from the air-freshener.

The effectiveness of the solubilized perfume to freshen the surrounding air in rooms, shops, airports and other open spaces, as well as closed spaces such as cupboards, drawers and closets, is thus significantly and unexpectedly improved by the presence of the solubilizing-aid ingredient.

According to a particular embodiment of the invention, suitable such salts are selected from the group consisting of sodium, potassium, magnesium and calcium salts of pyridine carboxylic acids, proline acid, pyrrolidone carboxylic acid, benzoic acid, hydroxyl-benzoic acid, amino-benzoic acid, L-lactic acid, L-ascorbic acid, bicarbonate, halide, succinic acid, oxalic acid, tartaric acid, citric acid, a $C_8$-$C_{10}$ derivative of benzoic, hydroxyl-benzoic or amino-benzoic acid substituted by one or two $C_1$-$C_3$ alkyl groups (such as the sodium salt of p-methyl-benzoic acid or of p-isopropyl-hydroxyl-benzoic acid), benzene-sulfonic acid, a $C_7$-$C_9$ benzene-sulfonic acid substituted by one or two methyl or ethyl groups (such as potassium toluene sulfonate), optionally hydroxylated naphthalene-sulfonic acid, an optionally hydroxylated $C_{11}$-$C_{16}$ naphthalene-sulfonic acid substituted by one or two $C_1$-$C_5$ alkyl groups (such as sodium butylnaphtalene sulfonate), $C_3$ to $C_6$ alkanoic acids (such as the sodium salt of pentanoic acid), and any mixture of said salts.

In particular, the solubilizing-aid ingredient may be advantageously chosen amongst the following compounds: pyrrolidone carboxylic acid sodium salt (also known as AJIDEW® NL-50 from Ajinomoto), sodium benzoate, sodium L-lactate, calcium L-ascorbate, sodium bicarbonate and di-sodium succinate. Any mixtures of said salts can also be used.

The solubilizing-aid ingredient is present in an amount of at least 0.01% by weight, relative to the total weight of the liquid composition.

According to particular embodiments of the invention, the amount of solubilizing—aid ingredient will be comprised between 0.1 and 10% w/w, the exact amount thereof to obtain a clear composition and an improved air-freshener according to the invention depending on the exact nature of the perfume oil, on the oil-solubilizer or surfactant mixture, in particular on the w/w ratio of ionic and non-ionic fractions thereof, as the case may be, and on the amount of perfume oil present. However, in general and according to particular embodiments, said amount is advantageously comprised between 0.1 and 5% w/w, or even between 0.1 and 2% w/w, relative to the total weight of the liquid nano-dispersion.

In a general manner, the solubilizing-aid ingredient is used in amounts such the ratio (S+SA)/O is comprised between 0.2 and 10, for a (surfactant system)/oil ratio comprised between 0.3 and 1.4. Preferred compositions display an oil/solubilizing system ratio above 1.0, preferably above 1.5 or even 2.0.

Concerning the fourth component of the present airfreshener liquid composition, i.e. water, it is useful to mention that it is preferable to use de-ionized water.

The invention's clear liquid composition can also comprise, as optional components, one or more ingredients such as colorants or dyes, anti-microbial agents, antioxidants, preservatives, chelating agents, bittering agents or UV-inhibitors. Many of these of materials are well known to a person skilled in the art Whenever said ingredients are added to the clear liquid air-freshening compositions, then they will represent no more than 3% w/w, or even 2% w/w, the percentages being relative to the total weight of the composition.

Water soluble dyestuffs suitable for the present invention can be found in the Colour Index International published by The Society of Dyers and Colourists. The inclusion levels of suitable dyestuffs is typically between 0.005 to 0.5% w/w. Non-limiting examples of dyes suitable for the present invention include: Vitasyn Quinoline Yellow 70, C.I. No. 47005; Vitasyn Tartrazine X 90, C.I. No. 19140; Sanolin Yellow BG, C.I. No. 19555; Vitasyn Orange RGL 90, C.I. No. 15985; Vitasyn Ponceau 4RC 82, C.I. No. 16255; Sanolin Red NBG, C.I. No. 18134; Sanolin Rhodamin B, C.I. No. 45100; Sanolin Violet E2R; Sanolin Violet FBL; Duasyn Ink Blue SLK, C.I. No. 42780; Nylosan Blue PRL 200, C.I. No. 62058;

Sanolin Blue NBL, C.I. No. 61585; Duasyn Acid Blue AE 02, C.I. No. 42090; Vitasyn Blue AE 90, C.I. No. 42090; Sanolin Green R-3GL; Sanolin Green 6GLN. All dyestuffs origin: Clariant.

The inclusion of a bittering agent in the composition is also desirable as this renders the product unpalatable, making it less likely that to be ingested, especially by young children. One such suitable bittering agent is Bitrex™ (denatonium benzoate, origin: Macfarlan Smith Ltd.). Typically the inclusion level of Bitrex™ is from 10 to 500 ppm. Other suitable bittering agents include, but are not limited to, isopropyl alcohol, methyl ethyl ketone and methyl n-butyl ketone, at a typical inclusion level from 0.5 to 5% w/w.

Non-limiting examples of other water soluble ingredients that may be added to the composition include one or more of the following: ethanol; isopropanol; ethylene glycol; propylene glycol; diethylene glycol; dipropylene glycol; propylene glycol monomethyl ether; dipropylene glycol monomethyl ether; tripropyleneglycol monomethyl ether; propylene glycol n-butyl ether; dipropylene glycol n-butyl ether; tripropylene glycol n-butyl ether, propylene glycol n-propyl ether; dipropylene glycol n-propyl ether; Eastman EP (origin: Eastman Chemical Company); Eastman EB (origin: Eastman Chemical Company); Eastman EEH (origin: Eastman Chemical Company); Eastman DM (origin: Eastman Chemical Company); Eastman DE (origin: Eastman Chemical Company); Eastman DP (origin: Eastman Chemical Company); Eastman DB (origin: Eastman Chemical Company).

Non-limiting examples of other oil soluble ingredients that may be added to the composition include one or more of the following: isoparaffins (e.g. Isopar H, Isopar J, Isopar K, Isopar L, Isopar M, Isopar P, Isopar V (all origin: Exxon Chemical)); normal paraffins (e.g. Norpar 12, Norpar 15 (all origin: Exxon Chemical)); dearomatised hydrocarbons (e.g. Exxsol D 155/170, Exxsol D 40, Exxsol D 180/200, Exxsol D 60, Exxsol D 70, Exxsol D 80, Exxsol D 100, Exxsol D 110, Exxsol D 120 (all origin: Exxon Chemical)); isopropyl myristate; diethyl phthalate.

The liquid composition of the invention, when incorporated in an air freshening device, allows an improved performance thereof relative to prior known wick devices, as will become apparent from the examples presented further on.

The perfume composition of the invention is a clear, water-based thermodynamically stable isotropic nano-dispersed system in which high amounts of almost any perfume or perfume composition can be easily solubilized in an external water-phase with significantly lower levels of surfactant than that employed in conventional air freshener formulae. Usually and preferably the weight ratio between surfactant(s) and perfume is less than 1. The compositions display excellent transparency and stability over large temperature domains.

By "clarity" we mean here the measure of the light scattered, at an angle of 90°, by the invention's perfume compositions. According to prized embodiments of the invention, the composition has clarity or transparency comprised between 0 and 90 NTU (Nepholemetric Turbidity Units), preferably between 0 and 50 NTU, when measured between 400 and 600 nm in a 2.5 cm cell at 25 C.

The invention's compositions can be prepared according to any method known in the art. A suitable method consists in dissolving into the water the surfactant or perfume solubilizing system, to form a clear micellar solution which acts as a pre-microemulsion. Possibly, during this stirring stage a nitrogen blanket may be useful to avoid foaming and to protect the system from oxygen contamination. To the resulting clear micellar solution is added under gentle stirring the fragrance oil such that a milky emulsion results. Finally the latter is turned into an isotropic clear, single-phase product by addition of the solubilizing-aid ingredient, and whenever necessary the optional ingredients to form a clear dispersion.

According to another suitable method, one can proceed by dissolving into the water the surfactant system, to form a clear micellar solution. To the resulting micellar solution are added under gentle stirring the solubilizing-aid ingredient, and whenever necessary the optional ingredients to form an initial oil-free microemulsion. Under gentle mixing the resulting oil-free microemulsion can easily solubilize the corresponding amount of oil, namely the perfume, to form an isotropic clear, single-phase product. High mechanical forces such as shear forces are not necessary to manufacture the present air freshener compositions.

Usually a clear product is obtained in a short time, less than 30 min stirring, and sometimes even instantly.

The inclusion of the solubilizing-aid ingredient(s) is an important feature of the invention. A surprising interfacial synergistic mechanism between the surfactant(s) and the solubilizing-aid ingredient(s) boosts the solubilization capacity of the surfactant system. Surfactant formulations without such solubilizing-aid ingredient display limited solubilization capacity and are selective to the perfume composition. Thus, some performing attributes of the said formulations, such as clarity and temperature stability, very much depend on the surfactant system and often require the use of high amounts of the latter.

The invention's liquid perfume compositions also display very good stability, e.g. phase separation is not observed within a reasonable frame of time. Indeed, they are commonly stable for at least 30 days, at temperatures comprised between 2° and 60° C. Furthermore, in some cases nearly thermodynamic stability, e.g. more than 6 months at temperatures comprised between 2° and 45° C., was achieved.

However, it has to be mentioned that the range of temperatures in which they show very good stability is a function of the amount, as well as the exact nature, of the perfume oil, the oil-solubilizing or surfactant system and solubilizing-aid ingredient used. Therefore in some cases it is possible that the stability temperature range of the named microemulsions may be narrower, e.g. from 5° to 45° C. only, or wider, e.g. from 0° to 80° C.

The preferred use of the liquid composition is in conventional liquid wick air fresheners; this means any air freshener dispenser that comprises a reservoir containing the fragrance solution, into which dips a porous wick which is connected to an emanating surface (often the wick and emanating surface are the same component). Such dispensers are widely used in the field of air freshening. Non-limiting examples of suitable dispensers are described in the following publications: U.S. Pat. No. 4,928,881; U.S. Pat. No. 4,739,928; WO 2004/110559, the contents of which are hereby included by reference. More detailed description of such devices is not warranted here, the skilled person being well able to realize such devices according to generally known methods and resorting to the use therein of the liquid compositions described above.

The composition may also be used in other air freshener devices. Non-limiting examples of other dispensers that could be used include wick air freshener liquid dispensers that comprise a non-porous wicking function, as described in U.S. Pat. No. 5,875,968, and PCT applications WO 98/25651 and WO 98/26809 for instance. In such examples the perfume solution is transported to the emanating surface via a non-porous capillary rather than a wick.

Other suitable air freshening devices comprising one or more external capillary members to transport the fragrance from the reservoir are described in WO 89/08462.

Other suitable dispensers that comprise a piezoelectric actuator or other means of atomizing and diffusing the fragrance solution into the surroundings, include but are not limited to those dispensers described for example in US 2003/0080214, US 2003/0066904, WO 02/068128, EP 1 502 608, WO 02/034409. We have in fact surprisingly established that the perfume compositions of the invention display a viscosity which is significantly lower than that of conventional air freshener compositions, such that atomization of the instant perfume compositions, and thus diffusion thereof in the air freshener surroundings, significantly improved.

The contents of all these publications mentioned above, which relate to the realization and components of the described air freshener devices, are hereby included by reference.

The compositions of the invention, when applied to conventional liquid wick air freshening devices, provide more linear release of the perfume than conventional formulae. Towards the end of the expected life span of the product, the rate of evaporation from devices employing the composition of the invention is approximately twice that of those in which conventional formulae are used, as will become apparent from the examples presented below. There is an associated improvement in fragrance intensity during the life of the product. Surprisingly, with some fragrances, this performance benefit is perceived throughout the whole life of the product, and not only at the end of life when the reduction in performance of the conventional formulae due to wick clogging would be more apparent.

Moreover, the perfume compositions of the invention are non-toxic and safe for use, as well as cost-effective, thus rendering the air freshener devices particularly attractive and advantageous over prior known devices.

In addition to the perfuming ingredients as defined above, the perfume compositions of the invention may also contain other common air deodorizing, antibacterial or freshening ingredients, if it is desired to deodorize or purify the ambient air.

An additional benefit is that it is more obvious to the user when the invention's device is exhausted and should be replaced. In devices employing conventional formulae the wick may be more or less completely saturated with non-volatile surfactant(s) and the reservoir therefore retains liquid long after the performance of the product reaches an unacceptable level of effectiveness. The user thus maintains the conventional devices in use long after they are of any utility. The reduced surfactant level in the composition of the invention helps ensure that the reservoir appears empty of liquid after the appropriate period of use, thus signaling need for replacement.

The nature and type of the constituents of the consumer product do not warrant a more detailed description here, which in any case would not be exhaustive, the skilled person being able to select them on the basis of its general knowledge and according to the nature and the desired effect of said product.

A further object of the present invention is the use of the air freshener of the invention to confer, enhance, improve, modify or freshen the odor and ambient air quality of a room, an open space, a closet or other closed space, via activation therein of the device to expose its surroundings to the perfume diffused.

The invention also relates to the use of the above-described liquid compositions to confer, enhance, improve, modify or freshen the odor and ambient air quality of a room, an open space, closet or other closed space.

EXAMPLES

The following examples are further illustrative of the present invention embodiments, and further demonstrate the advantages of the invention devices relative to prior art teachings.

Comparative Example 1A

A conventional hydro-alcoholic composition for use in wick air freshener was prepared with the following ingredients.

TABLE 1

| Conventional formulation | |
| --- | --- |
| Ingredient | % w/w |
| Perfume Base | 6.00 |
| CREMOPHOR ® RH40[1] | 12.00 |
| Isopropanol[2] | 12.00 |
| Deionised Water | 70.00 |
| | 100.00 |

[1]PEG-40 Hydrogenated Castor Oil, origin: BASF GmbH.
[2]Origin: Sigma-Aldrich

The conventional air freshener composition was obtained according to the formula given in Table 1 by admixing, in a first step, the surfactant, perfume base (PURE CITRUS 163641, origin: Firmenich SA) and isopropanol in a beaker. This mixture was gently stirred at ambient temperature for a few minutes by means of a magnetic bar stirrer. In a second step, the deionised water was added to the beaker under stirring. A clear product was instantly formed. Following this procedure a formulation having a surfactant/perfume ratio of 2.0 was obtained.

Comparative Example 1B

A conventional hydro-alcoholic composition was prepared according to the formulation and procedure described in the Comparative Example 1A. In this case the perfume base was BLACK BEAUTY 150928; origin: Firmenich SA.

Following the same procedure described above, a formulation having a typical surfactant/perfume ratio of 2.0 was obtained.

Comparative Example 1C

A conventional hydro-alcoholic composition was prepared according to the formulation and procedure described in the Example 1A. In this case the perfume base was PAPAYA STAR 225263; origin: Firmenich SA.

Following the same procedure a formulation having a typical surfactant/perfume ratio of 2.0 was obtained.

Example 2A

Preparation of a Liquid Composition, According to the Invention, for Use in a Wick-Type Air Freshener In a first step, a surfactant-water base was prepared based on the formulation described in Table 2 below. All the ingredients were mixed together in a beaker and gently stirred at room temperature. After their complete dissolution, a clear micellar solution resulted.

TABLE 2

Surfactant-water base pre-formulation according to the invention

| Ingredient | % w/w |
|---|---|
| Aerosol OT-100[1] | 5.60 |
| GLYCOSPERSE ® O-20[2] | 2.15 |
| GLYCOSPERSE ® L-20[3] | 0.25 |
| Solubilisant LRI[4] | 3.34 |
| Deionised Water | 88.66 |
| | 100.00 |

[1] Dioctyl sulfosuccinate sodium salt; origin: Cytec Industries, Inc.
[2] Monooleate ethoxylated sorbitol with 20 EO; origin: Lonza Inc.
[3] Monolaureate ethoxylated sorbitol with 20 EO; origin: Lonza Inc.
[4] PPG-26 Buteth-26 & PEG-40 Hydrogenated Castor Oil & Water; origin: LWR Inc.

In a second step, an air freshener composition was obtained according to the formula given in Table 3. The above-described surfactant-water base, perfume base and solubilizing-aid ingredient were mixed together in a beaker. This mixture was gently stirred at ambient temperature for a few minutes by means of a magnetic bar stirrer. A translucent liquid crystal phase formed. In the next step, by water dilution, a clear product was instantly formed.

TABLE 3

Liquid formulation according to the invention

| Ingredient | % w/w |
|---|---|
| Surfactant-water base | 44.35 |
| Perfume Base[1] | 6.00 |
| AJIDEW ® N-50[2] | 0.35 |
| Sodium Benzoate | 0.10 |
| Deionised Water | 49.20 |
| | 100.00 |

[1] PURE CITRUS 163641; origin: Firmenich SA.
[2] Sodium Pyrrolidone Carboxylic Acid 50% aqueous solution; origin: Ajinimoto Inc.

Following this procedure a formulation having a surfactant/perfume ratio of 0.84 was obtained.

Example 2B

Preparation of a Liquid Composition, According to the Invention, for Use in a Wick Air Freshener In the first step, a surfactant-water pre-formulation base was prepared according to the formulation and procedure described in the Example 2A.

In the second step, an air freshener liquid composition was obtained according to the formula given in Table 4. The surfactant-water pre-formulation, perfume base and solubilizing-aid ingredient were mixed together in a beaker. This mixture was gently stirred at ambient temperature for a few minutes by means of a magnetic bar stirrer. A translucent liquid crystal phase formed. In the next step, by water dilution, a clear product was instantly formed.

TABLE 4

Liquid formulation according to the invention

| Ingredient | % w/w |
|---|---|
| Surfactant-water base | 44.35 |
| Perfume Base[1] | 6.00 |
| AJIDEW ® N-50 | 0.25 |
| Sodium Benzoate | 0.07 |
| Deionised Water | 49.33 |
| | 100.00 |

[1] BLACK BEAUTY 150928; origin: Firmenich SA

Following this procedure a formulation having a surfactant/perfume ratio of 0.84 was obtained.

Example 2C

Preparation of a Liquid Composition, According to the Invention, for Use in a Wick Air Freshener In the first step, a surfactant-water base was prepared according to the formulation and procedure described in the Example 2A.

In the second step, an air freshener composition was obtained according to the formula given in Table 5. The surfactant-water base, perfume base and solubilizing-aid ingredient were mixed together in a beaker. This mixture was gently stirred at ambient temperature for a few minutes by means of a magnetic bar stirrer. A translucent liquid crystal phase formed. In the next step, by water dilution, a clear product was instantly formed.

TABLE 5

Liquid formulation according to the invention

| Ingredient | % w/w |
|---|---|
| Surfactant-water base | 44.18 |
| Perfume Base[1] | 6.00 |
| AJIDEW ® N-50 | 0.11 |
| Sodium Benzoate | 0.07 |
| Deionised Water | 49.64 |
| | 100.00 |

[1] PAPAYA STAR 225263; origin: Firmenich SA.

Following this procedure a formulation having a surfactant/perfume ratio of 0.84 was obtained.

Example 3A

Comparative Evaporation Experiment of a Conventional Hydro-Alcoholic Composition and a Liquid Composition According to the Invention, Upon Use in a Wick Air Freshener All evaporation experiments were conducted in a conventional air freshener dispenser comprising a glass reservoir, a polyester wick, and a ventilated cover. Three conventional dispensers were each filled with 75 g of the conventional hydro-alcoholic formulation described in Comparative Example 1A, and the total mass of each device recorded.

A further three such dispensers were each filled with 75 g of the invention's liquid composition described in Example 2A, and the total mass of each such air freshener device according to the invention recorded.

All air freshener devices were placed in a temperature and humidity controlled test room (at 20° to 22° C. and 45% to 55% relative humidity) and the total mass of each was recorded at regular intervals, during a time period of up to 49 days.

The average cumulative weight loss recorded for the conventional air freshener, and for the invention air freshener, during the test period are listed in Table 6.

TABLE 6

Evaporation of liquid compositions from wick air freshener as a function of time

| Elapsed Time/days | Cumulative Weight Loss/g Invention Formulation of Example 2A | Cumulative Weight Loss/g Conventional formulation of Comp. Example 1A |
|---|---|---|
| 0 | 0.00 | 0.00 |
| 7 | 14.60 | 19.28 |
| 14 | 25.01 | 30.16 |
| 21 | 33.30 | 36.74 |
| 28 | 40.14 | 41.10 |
| 35 | 46.06 | 44.41 |
| 42 | 51.56 | 47.25 |
| 49 | 56.88 | 49.75 |

The data is represented graphically in FIG. 1. It can be seen that the evaporation profile of the invention's liquid formulation is more linear over the lifetime of the product than that of the conventional air freshener composition.

Figure 2:
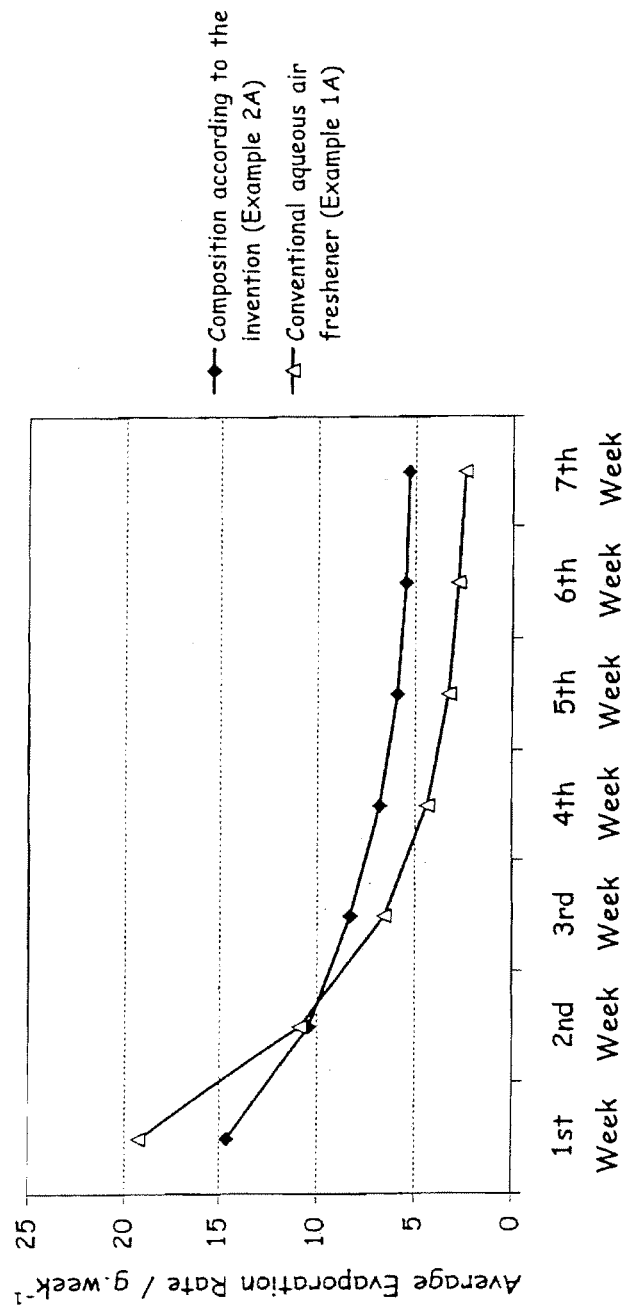
FIG. 2 shows the average weekly rate of emanation of a composition according to the invention (of Example 2A) compared to a conventional aqueous based air freshener (of Comparative Example 1A) over a period of time.

This is further confirmed by reference to Table 7 below and FIG. 2, which show the average mass of liquid composition evaporated during each week of use. Due to the difference in composition between the two formulations the rate of release of the invention's formulation is more consistent than that of the conventional formulation. The average rate of evaporation of liquid from the formulation according to the invention, in the first 2 weeks of use, is less than that from the conventional formulation. After 3 weeks of use, the rate of evaporation from the invention's formulation is higher than that of the conventional formulation. In the $7^{th}$ week of use, the rate of evaporation from the formulation according to Example 2A is more than twice that of the conventional formulation.

TABLE 7

Average mass of perfume composition evaporated during each week of use

| Time Period | Average Weight Loss During Specified Time Period/g Invention formulation of Example 2A | Average Weight Loss During Specified Time Period/g Conventional formulation of Comp. Example 1A |
|---|---|---|
| 1st Week | 14.60 | 19.28 |
| 2nd Week | 10.41 | 10.88 |
| 3rd Week | 8.29 | 6.58 |
| 4th Week | 6.83 | 4.36 |
| 5th Week | 5.92 | 3.31 |
| 6th Week | 5.50 | 2.84 |
| 7th Week | 5.32 | 2.50 |

Furthermore, almost 15% more liquid is released, over the same period of use, from the air freshener containing the invention's formulation than from that carrying the conventional formulation. The glass reservoir containing the formulation according to Example 2A of the invention appears completely empty and thereby provides the user with a visual indication that the product has reached the end of its useful life. The reservoir containing the conventional formulation of Example 1A still contained a significant and visible amount of a viscous liquid.

Example 3B

Comparative Evaporation Experiment of a Conventional Hydro-Alcoholic Composition and a Liquid Composition According to the Invention, Upon Use in a Wick Air Freshener The experiment was carried out according to the procedure described in Example 3A, using 3 replicates of the conventional air freshener composition prepared in Comparative Example 1B and 3 replicates of the invention formulation prepared in Example 2B.

Figure 3:
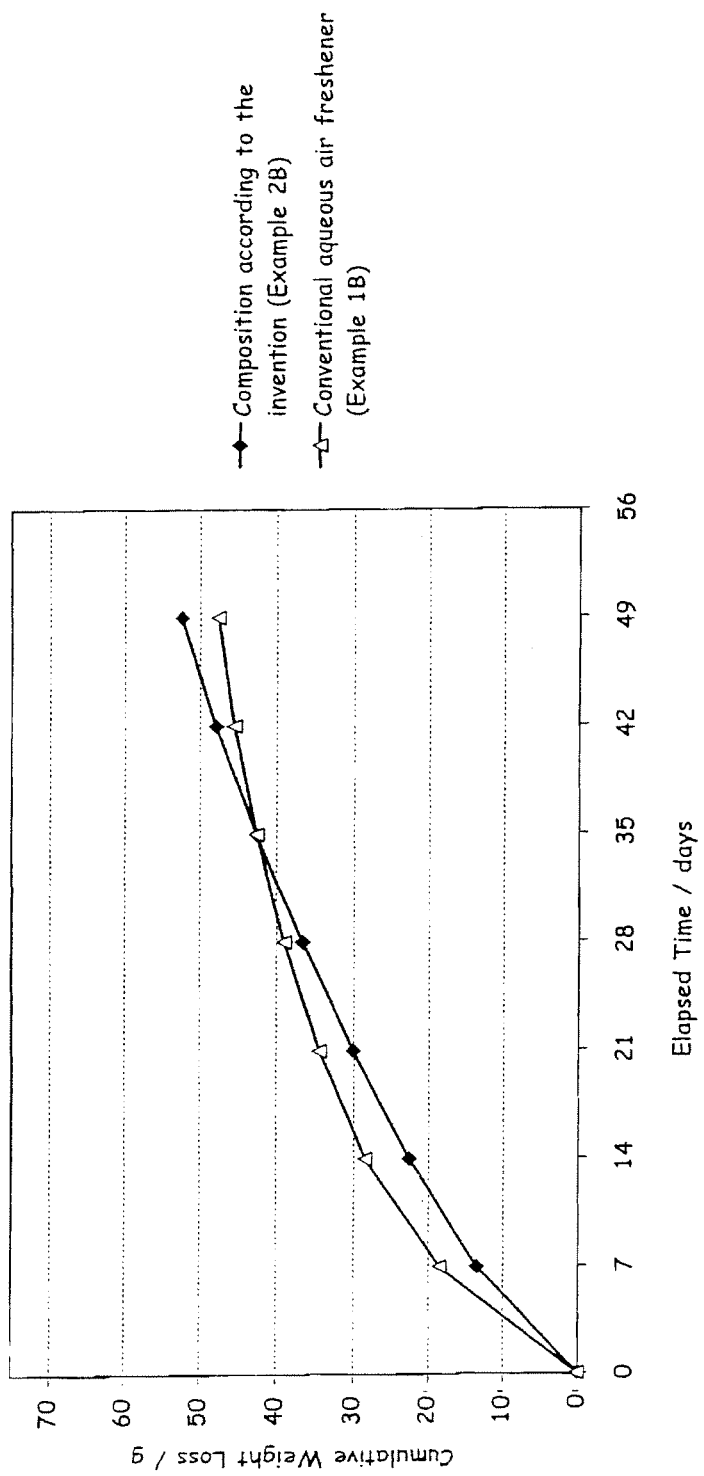
FIG. 3 shows the cumulative weight loss of a composition according to the invention (of Example 213) compared to a conventional aqueous based air freshener (of Comparative Example 1B) over a period of time.
Figure 4:
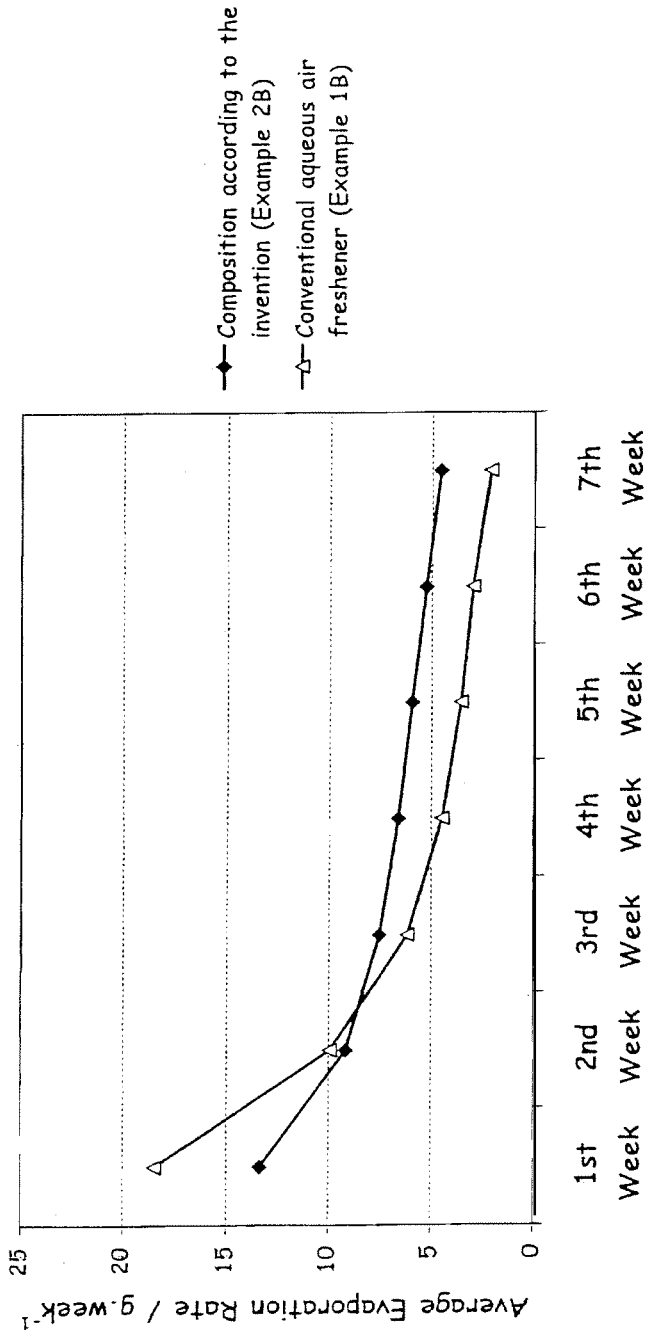
FIG. 4 shows the average weekly rate of emanation of a composition according to the invention (of Example 2B) compared to a conventional aqueous based air freshener (of Comparative Example 1B) over a period of time.

The cumulative weight loss during use is listed in Table 8 and represented graphically in FIG. 3. Table 9 and FIG. 4 show the average mass of liquid composition evaporated during each week of use.

TABLE 8

Evaporation of liquid compositions from wick air freshener as a function of time

| Elapsed Time/days | Cumulative Weight Loss/g Invention Formulation of Example 2B | Cumulative Weight Loss/g Conventional formulation of Comp. Example 1B |
|---|---|---|
| 0 | 0.00 | 0.00 |
| 7 | 13.36 | 18.42 |
| 14 | 22.51 | 28.36 |
| 21 | 30.03 | 34.49 |
| 28 | 36.62 | 38.97 |
| 35 | 42.55 | 42.51 |
| 42 | 47.81 | 45.46 |
| 49 | 52.37 | 47.53 |

TABLE 9

Average mass of liquid composition evaporated during each week of use

| Time Period | Average Weight Loss During Specified Time Period/g Invention formulation of Example 2B | Average Weight Loss During Specified Time Period/g Conventional formulation of Comp. Example 1B |
|---|---|---|
| 1st Week | 13.36 | 18.42 |
| 2nd Week | 9.15 | 9.94 |
| 3rd Week | 7.51 | 6.13 |
| 4th Week | 6.60 | 4.48 |
| 5th Week | 5.93 | 3.55 |
| 6th Week | 5.26 | 2.94 |
| 7th Week | 4.57 | 2.07 |

Due to the difference in composition between the two formulations the rate of release of the invention's formulation is more consistent than that of the conventional formulation. In the $7^{th}$ week of use, the rate of evaporation from the formulation according to Example 2B is more than twice that of the conventional formulation.

Furthermore, greater than 10% more liquid is released, over the same period of use, from the air freshener containing the invention's formulation than from that carrying the conventional formulation. The glass reservoir containing the formulation according to Example 2B of the invention appears completely empty and thereby provides the user with a visual indication that the product has reached the end of its useful life. The reservoir containing the conventional formulation of Example 1B still contained a significant and visible amount of a viscous liquid.

Example 3C

Comparative Evaporation Experiment of a Conventional Hydro-Alcoholic Composition and a Liquid Composition According to the Invention, Upon Use in a Wick Air Freshener The experiment was carried out according to the procedure described in Example 3A, using 3 replicates of the conventional air freshener composition prepared in Comparative Example 1C and 3 replicates of the invention formulation prepared in Example 2C.

Figure 5:
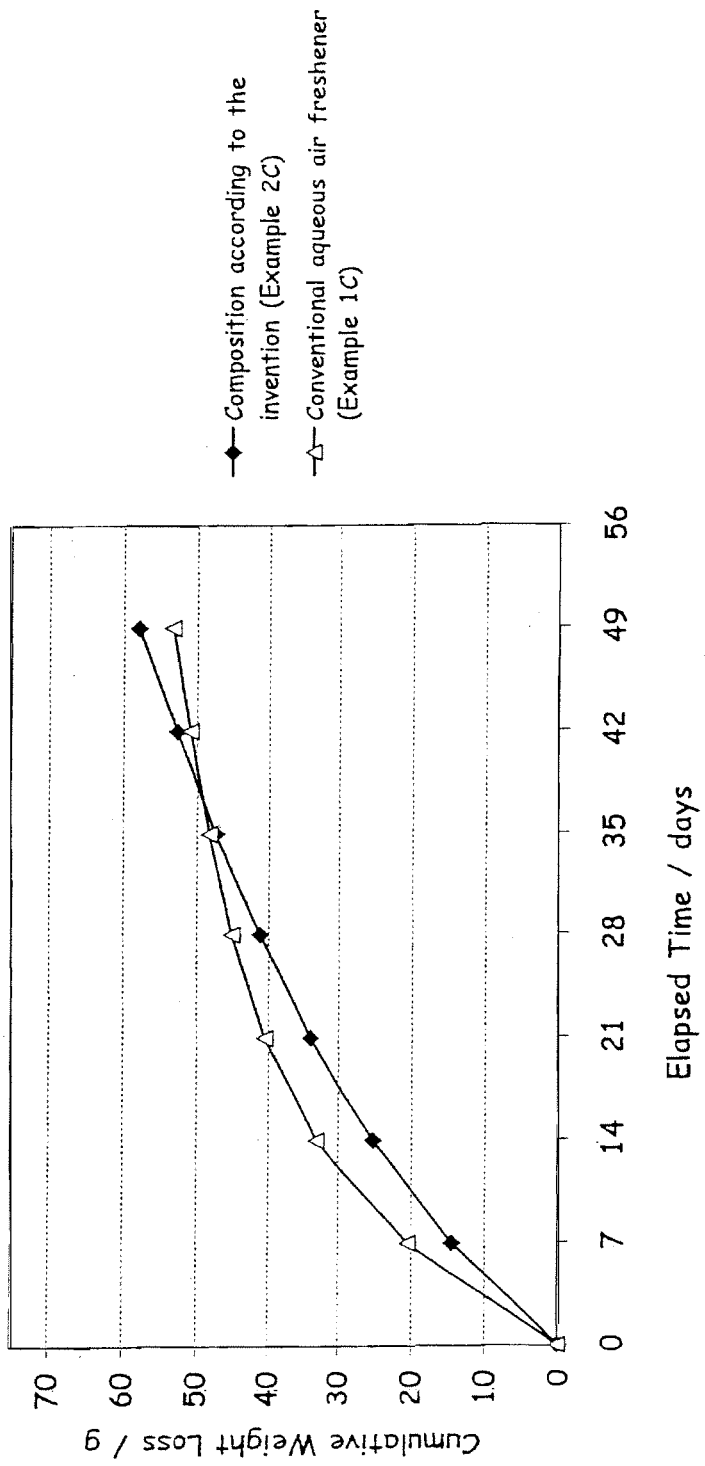
FIG. 5 shows the cumulative weight loss of a composition according to the invention (of Example 2C) compared to a conventional aqueous based air freshener (of Comparative Example 1C) over a period of time.

The cumulative weight loss during use is listed in Table 10 and represented graphically in FIG. 5. Table 11 and FIG. 6 show the average mass of liquid composition evaporated during each week of use.

TABLE 10

Evaporation of liquid compositions from wick air freshener as a function of time

| Elapsed Time/days | Cumulative Weight Loss/g Invention Formulation of Example 2C | Cumulative Weight Loss/g Conventional formulation of Comp. Example 1C |
| --- | --- | --- |
| 0 | 0.00 | 0.00 |
| 7 | 14.27 | 20.47 |
| 14 | 25.31 | 33.14 |
| 21 | 34.04 | 40.51 |
| 28 | 41.18 | 45.06 |
| 35 | 47.29 | 48.21 |
| 42 | 52.75 | 50.94 |
| 49 | 57.88 | 53.45 |

TABLE 11

Average mass of liquid composition evaporated during each week of use

| Time Period | Average Weight Loss During Specified Time Period/g Invention formulation of Example 2C | Average Weight Loss During Specified Time Period/g Conventional formulation of Comp. Example 1C |
| --- | --- | --- |
| 1st Week | 14.27 | 20.47 |
| 2nd Week | 11.04 | 12.67 |
| 3rd Week | 8.73 | 7.37 |
| 4th Week | 7.14 | 4.54 |
| 5th Week | 6.11 | 3.15 |
| 6th Week | 5.46 | 2.73 |
| 7th Week | 5.13 | 2.51 |

Due to the difference in composition between the two formulations the rate of release of the invention's formulation is more consistent than that of the conventional formulation. In the 7th week of use, the rate of evaporation from the formulation according to Example 2C is more than twice that of the conventional formulation of Comparative Example 1C. Furthermore, greater than 8% more liquid is released, over the same period of use, from the air freshener containing the invention's formulation than from that carrying the conventional formulation. Both reservoirs appeared empty.

Example 4A

Quantitative Sensory Testing of a Conventional Hydro-Alcoholic Composition and a Liquid Composition According to the Invention, in a Wick Air Freshener All sensory testing was conducted with conventional air freshener dispensers comprising a glass reservoir, a polyester wick, and a ventilated cover.

Two such dispensers were each filled with 75 g of the conventional hydro-alcoholic formulation described in Comparative Example 1A.

A further two such dispensers were each filled with 75 g of the invention's composition described in Example 2A.

The samples were presented to panelists in 21 $m^3$ odor evaluation chambers. Each chamber was labeled with a randomly generated three digit code. The temperature and humidity conditions were controlled to 20-22° C. and 45-55% relative humidity respectively. The test samples were placed in the center of the chamber 60 minutes prior to evaluation and hidden from view. All evaluations were made within a 30 minute period, following the equilibration time in the booths.

Each evaluation session was attended by 20 to 24 panelists. The panelists had previously been screened for olfactive acuity, and were experienced in rating the performance of air freshener products.

The odor in the chambers was evaluated through a small port. The chambers were evaluated in a randomized and balanced order.

Panellists were asked to rate the overall fragrance intensity on a graduated 7-point line scale, in increasing odor intensity, from 1=odorless to 7=extremely strong odor. The data generated from the panel was statistically analyzed using analysis of variance (ANOVA) and least significance difference (LSD, $\alpha$=0.05), based on the results of both replicates at each time point.

Between evaluation sessions the samples were placed in a temperature and humidity controlled test room (at 20° to 22° C. and 45% to 55% relative humidity). The results of the sensory evaluations are listed in Table 12.

TABLE 12

Sensory evaluation of the liquid wick air freshener formulation described in Comparative Example 1A (conventional formulation) and Example 2A (invention formulation)

| Sample Age/days | Average Mean Panel Intensity - Invention Formulation of Ex. 2A | Average Mean Panel Intensity - Conventional Formulation of C. Ex. 1A | ANOVA[1) |
| --- | --- | --- | --- |
| 0 | 4.08 | 3.82 | NSD |
| 7 | 3.81 | 3.31 | * |
| 13 | 4.38 | 4.31 | NSD |
| 28 | 3.66 | 2.95 | * |
| 34 | 3.25 | 2.78 | * |
| 42 | 3.45 | 2.92 | * |

NSD = no significant difference;
*= significant difference at 5% level

This data supports the superior performance observed with the present invention formulation compared to the conventional formulation.

Example 4B

Quantitative Sensory Testing of a Conventional Hydro-Alcoholic Composition and a Liquid Composition According to the Invention, in a Wick Air Freshener Similar sensory evaluations were carried out according to the procedure described in Example 4A, using 2 replicates of the conventional air freshener composition prepared in Comparative Example 1B and 2 replicates of the invention formulation prepared in Example 2B. The results of the sensory evaluations are listed in Table 13.

TABLE 13

Sensory evaluation of the liquid wick air freshener formulation described in Comparative Example 1B (conventional formulation) and Example 2B (invention formulation)

| Sample Age/ days | Average Mean Panel Intensity - Invention Formulation of Ex. 2B | Average Mean Panel Intensity - Conventional Formulation of C. Ex. 1B | ANOVA[1] |
|---|---|---|---|
| 0 | 3.92 | 4.21 | NSD |
| 7 | 3.74 | 3.53 | NSD |
| 13 | 2.89 | 2.96 | NSD |
| 28 | 3.35 | 2.97 | * |
| 34 | 3.41 | 3.18 | NSD |
| 42 | 3.58 | 3.10 | * |

NSD = no significant difference;
*= significant difference at 5% level

This data supports the superior performance observed with the present invention formulation compared to the conventional formulation.

Example 5

Comparative Solubilization Capacity of Conventional Hydro-Alcoholic Compositions and a Nanofresh™ Microemulsion Composition A perfume base composition comprising the ingredients described in Table 14 was prepared.

TABLE 14

Perfume Base

| Ingredient | % w/w | cLogP[1] |
|---|---|---|
| Geranyl acetate | 5 | 4.48 |
| Terpinyl acetate | 10 | 4.34 |
| 9-Undecenal | 1 | 4.04 |
| Allyl 3-cyclohexylpropanoate | 7 | 3.85 |
| HABANOLIDE ®[2] | 15 | 4.88 |
| ISO E SUPER ®[3] | 10 | 5.18 |
| LILIAL ®[4] | 5 | 4.36 |
| Limonene | 4 | 4.83 |
| cis-3-Hexenol | 3 | 1.61 |
| Hexyl salicylate | 10 | 5.06 |
| VERDOX ®[5] | 30 | 4.42 |

[1] cLogP is the estimated logarithmic octanol-water partition coefficient for the ingredient.
[2] Oxacyclohexadec-13-en-2-one; origin: Firmenich S.A.
[3] 1,2,3,4,5,6,7,8-Octahydro-1,1,6,7-tetramethyl-7-acetyl naphthalene; origin: International Flavors & Fragrances, Inc.
[4] p-t-Butyl-2-methyl propanal; origin: Givaudan-Roure, Switzerland.
[5] 2-t-Butyl cyclohexyl acetate; origin: International Flavors & Fragrances, Inc.

The octanol-water partition coefficient is a physical property used extensively to describe the lipophilic or hydrophobic properties of a chemical. It is the ratio of a chemical's concentration in the octanol-phase to its concentration in the aqueous phase of a two-phase system at equilibrium. Since actually measured values cover a very large range (at least 12 orders of magnitude), the corresponding logarithm (LogP) is commonly used to characterize its value.

LogP has been estimated using a fragment constant methodology. In a fragment constant method, a structure is divided into fragments (atom or larger functional groups) and coefficient values of each fragment or group are summed together to yield the LogP estimate or calculation (cLogP). This methodology is called the Atom/Fragment Contribution (AFC) method. These values are then improved by the addition of correction factors. Details of the method employed can be found in the following reference: Meylab, W. M. and Howard, P. H., Atom/fragment contribution method for estimating octanol-water partition coefficients. *J. Pharm. Sci.* 84: 83-92, 1995.

Conventional hydro-alcoholic compositions were prepared according to formulae detailed in Table 15 using the perfume base detailed in Table 14.

TABLE 15

Conventional hydro-alcoholic compositions

| Formulation | #1 | #2 | #3 | #4 | #5 | #6 | #7 |
|---|---|---|---|---|---|---|---|
| Perfume Base (% w/w) | 6 | 6 | 6 | 6 | 6 | 6 | 6 |
| Isopropanol (% w/w) | 12 | 12 | 12 | 6 | 6 | 6 | — |
| Cremophor RH40 (% w/w) | 12 | 9 | 6 | 12 | 9 | 6 | 12 |
| Deionised water (% w/w) | 70 | 73 | 76 | 76 | 79 | 82 | 82 |
| Surfactant/perfume ratio | 2.0 | 1.5 | 1.0 | 2.0 | 1.5 | 1.0 | 2.0 |

In a first step the surfactant, perfume base and isopropanol were mixed together in a beaker. This mixture was gently stirred at ambient temperature for a few minutes by means of a magnetic bar stirrer. In a second step the deionized water was added to the beaker under stirring.

The samples were stored in incubators at 3° C., 22° C. and 37° C. and their appearance assessed after 48 hours. The appearance of the samples at the specified storage conditions is given in Table 16.

TABLE 16

Appearance of conventional hydro-alcoholic formulations after 48 hours storage

| Formulation | #1 | #2 | #3 | #4 | #5 | #6 | #7 |
|---|---|---|---|---|---|---|---|
| 3° C. | cloudy | very cloudy | very cloudy | very cloudy | very cloudy | very cloudy | very cloudy |
| 22° C. | clear | slightly cloudy | very cloudy | cloudy | very cloudy | very cloudy | very cloudy |
| 37° C. | clear | slightly cloudy | very cloudy | cloudy | very cloudy | very cloudy | very cloudy |

A liquid composition, according to the invention, was prepared. In the first step, a surfactant-water base was prepared based on the formulation described in Table 17. All the ingredients were mixed together in a beaker and gently stirred at room temperature. After their complete dissolution a clear micellar solution resulted.

TABLE 17

Surfactant-Water base formulation according to the invention

| Ingredient | % w/w |
|---|---|
| Aerosol OT-100[1] | 5.60 |
| GLYCOSPERSE ® O-20[2] | 2.15 |
| GLYCOSPERSE ® L-20[3] | 0.25 |

TABLE 17-continued

Surfactant-Water base formulation according to the invention

| Ingredient | % w/w |
|---|---|
| Solubilisant LRI[4] | 3.34 |
| Deionised Water | 88.66 |
| | 100.00 |

[1] Dioctyl sulfosuccinate sodium salt; origin: Cytec Industries, Inc.
[2] Monooleate ethoxylated sorbitol with 20 EO; origin: Lonza Inc.
[3] Monolaureate ethoxylated sorbitol with 20 EO; origin: Lonza Inc.
[4] PPG-26 Buteth-26 & PEG-40 Hydrogenated Castor Oil & Water; origin: LWR Inc.

In the second step, the formula given in Table 18 was prepared. The surfactant-water base (Table 17), perfume base (Table 14), and solubilizing-aid ingredients were mixed together in a beaker. This mixture was gently stirred at ambient temperature for a few minutes by means of a magnetic bar stirrer. A translucent liquid crystal phase formed. Addition of the water yielded a clear product having a surfactant/perfume ratio of 1.00.

TABLE 18

Liquid formulation according to the invention

| Ingredient | % w/w |
|---|---|
| Surfactant-water base | 52.91 |
| Perfume Base | 6.00 |
| AJIDEW ® N-50[1] | 0.55 |
| Sodium Benzoate | 0.30 |
| Deionised Water | 40.24 |
| | 100.00 |

[1] Sodium Pirrolydone Carboxylic Acid 50% aqueous solution; origin: Ajinimoto Inc.

Samples of the invention's microemulsion composition were stored in incubators at 3° C., 22° C. and 37° C. and their appearance assessed after 48 hours. The samples remained clear under all test conditions.

Thus using the liquid composition of the invention, it is possible to produce aqueous formulations using perfumes with high cLogP, that are stable over a range of temperatures, using a substantially lower surfactant/perfume ratio than conventional air freshener formulae.

What is claimed is:

1. An air freshener device for perfuming or freshening the surroundings thereof, which comprises:
   A) a vessel carrying a liquid composition which contains:
      1) 0.5 to 40% w/w of a perfume;
      2) an oil-solubilizing system containing one or more surfactants of the non-ionic, anionic, cationic or amphoteric type, or a mixture thereof; and
      3) at least 40% weight of water;
      with the weight percentages being relative to the total weight of liquid composition;
   B) an emanating surface capable of providing for diffusion of said liquid composition;
   C) a wick for carrying the liquid composition from the container vessel to the emanating surface; and
   D) optionally, removable means for preventing diffusion of the liquid composition prior to the activation of the air freshener device by a user thereof;
      wherein said liquid composition further comprises a solubilizing-aid ingredient of pyrrolidone carboxylic acid sodium salt or a mixture of pyrrolidone carboxylic acid sodium salt with one or more salts selected from the group consisting of sodium benzoate, sodium L-lactate, calcium L-ascorbate, sodium bicarbonate, and di-sodium succinate.

2. An air freshener device according to claim 1, wherein the liquid composition comprises 0.01 to 10% w/w of solubilizing-aid ingredient.

3. An air freshener device according to claim 2, wherein the ratio of oil-solubilizing system to perfume is between 0.3 and 1.4.

4. An air freshener device according to claim 3, wherein the ratio of oil-solubilizing system to perfume is below 1.

5. An air freshener device for perfuming or freshening the surroundings thereof, which comprises:
   A) a vessel carrying a liquid composition which contains:
      1) 0.5 to 40% w/w of a perfume;
      2) an oil-solubilizing system containing one or more surfactants of the non-ionic, anionic, cationic or amphoteric type, or a mixture thereof, wherein the ratio of oil-solubilizing system to perfume is below 1;
      2) 0.01 to 10% w/w of a solubilizing aid ingredient of pyrrolidone carboxylic acid sodium salt or a mixture of pyrrolidone carboxylic acid sodium salt with one or more salts selected from the group consisting of sodium benzoate, sodium L-lactate, calcium L-ascorbate, sodium bicarbonate, and di-sodium succinate; and
      3) at least 40% weight of water;
      with the weight percentages being relative to the total weight of liquid composition;
   B) an emanating surface capable of providing for diffusion of said liquid composition;
   C) a wick for carrying the liquid composition from the container vessel to the emanating surface; and
   D) optionally, removable means for preventing diffusion of the liquid composition prior to the activation of the air freshener device by a user thereof.

6. An air freshener device according to claim 1, wherein the ratio between the amount of oil and the total amount of oil-solubilizing system plus solubilizing-aid ingredient is comprised between 0.1 and 5.

7. An air freshener device according to claim 5, wherein the ratio between the amount of oil and the total amount of oil-solubilizing system plus solubilizing-aid ingredient is comprised between 0.1 and 5.

8. An air freshener device according to claim 1, which comprises a surfactant system containing one or more anionic surfactants and one or more non-ionic surfactants.

9. An air freshener device according to claim 1, wherein
   a) the anionic surfactants are selected from the group consisting of sodium, potassium, ammonium and mono-, di- and tri-ethanolammonium salts of $C_6$-$C_{12}$ dialkyl sulfosuccinic acids, $C_7$-$C_{24}$ alkarylsulfonic acids, $C_6$-$C_{15}$ alkylsulfuric acid, $C_{10}$-$C_{20}$ acyl glutamic acid, and polyethylene glycol/dimethicone sulfosuccinic acids;
   b) the cationic surfactants are selected from the group consisting of halides, sulfates or carboxylates of $C_{20-30}$ quaternary ammonium alkyl, $C_{1-4}$ alkyl N-cocoyl-L-arginate, ($C_{10-20}$ amido) ($C_{1-4}$ alkyl) morpholine, IPDI copolymers with N—$C_{10-20}$ amido($C_{1-4}$ alkyl)-N—($C_{1-4}$ alkyl) ammonium, and polyethylene glycol/$C_{10}$-$C_{20}$ fatty alkyl amine/IPDI copolymers;
   c) the amphoteric surfactants are selected from the group consisting of $C_{10}$-$C_{20}$ fatty amido $C_2$-$C_5$ alkyl betaines, coco- and lauro-amphoacetates and the polyethylene glycol/$C_{10}$-$C_{20}$ fatty alkyl amine/glycine/IPDI copolymers;
   d) the non-ionic surfactants are selected from the group consisting of ethoxylated and propoxylated ($C_5$-$C_{12}$ alkyl)phenols ethers containing 5 to 20 EO or PO units, polyethylene glycol sorbitol ether containing 3 to 30 EO units, sucrose esters with $C_8$-$C_{20}$ fatty acid, ethoxylated aliphatic $C_6$-$C_{20}$ alcohols containing 2 to 30 EO units, $C_8$-$C_{20}$ polyglyceryl esters, polyethylene glycol and polypropylene glycol block copolymers, ethoxylated glycol ether containing 2 to 30 EO units, and polyethylene glycol mono- and -diester of aliphatic $C_5$-$C_{11}$ carboxylic acids containing 2 to 10 EO units.

10. An air freshener device according to claim 1, wherein the solubilizing-aid ingredient represents from 0.1 to 5% w/w of the liquid composition.

11. A method to confer, enhance, improve, modify or freshen the odor and ambient air quality of a room, an open space, a closet or other closed space, which consists in activating therein an air freshener device according to claim 1 to expose its surroundings to the perfume diffused by the activated air freshener.

12. An air freshener device according to claim 1, wherein the solubizing-aid ingredient is a mixture of pyrrolidone carboxylic acid sodium salt and sodium benzoate.

13. An air freshener device according to claim 5, wherein the solubizing-aid ingredient is a mixture of pyrrolidone carboxylic acid sodium salt and sodium benzoate.

14. An air freshener device according to claim 8, wherein
a) the anionic surfactants are selected from the group consisting of sodium, potassium, ammonium and mono-, di- and tri-ethanolammonium salts of $C_6$-$C_{12}$ dialkyl sulfosuccinic acids, $C_7$-$C_{24}$ alkarylsulfonic acids, $C_6$-$C_{15}$ alkylsulfuric acid, $C_{10}$-$C_{20}$ acyl glutamic acid, and polyethylene glycol/dimethicone sulfosuccinic acids; and
b) the non-ionic surfactants are selected from the group consisting of ethoxylated and propoxylated ($C_5$-$C_{12}$ alkyl)phenols ethers containing 5 to 20 EO or PO units, polyethylene glycol sorbitol ether containing 3 to 30 EO units, sucrose esters with $C_8$-$C_{20}$ fatty acid, ethoxylated aliphatic $C_6$-$C_{20}$ alcohols containing 2 to 30 EO units, $C_8$-$C_{20}$ polyglyceryl esters, polyethylene glycol and polypropylene glycol block copolymers, ethoxylated glycol ether containing 2 to 30 EO units, and polyethylene glycol mono- and -diester of aliphatic $C_5$-$C_{11}$ carboxylic acids containing 2 to 10 EO units.

* * * * *

UNITED STATES PATENT AND TRADEMARK OFFICE
CERTIFICATE OF CORRECTION

PATENT NO. : 8,474,732 B2  
APPLICATION NO. : 11/845566  
DATED : July 2, 2013  
INVENTOR(S) : O'Leary et al.

Page 1 of 1

It is certified that error appears in the above-identified patent and that said Letters Patent is hereby corrected as shown below:

In the Claims:

Column 22:
Line 19 (claim 5, line 9), before "0.01", change "2)" to -- 3) --.
Line 26 (claim 5, line 16), before "at least", change "3)" to -- 4) --.
Lines 58-59 (claim 9, lines 12-13), change "alkyl)-N—($C_{1-4}$ alkyl) ammonium," to
-- alkyl)-N,N-di($C_{1-4}$ alkyl)-N-($C_{1-4}$ alkyl) ammonium, --.

Signed and Sealed this  
Twentieth Day of August, 2013

Teresa Stanek Rea  
*Acting Director of the United States Patent and Trademark Office*